(12) United States Patent
Mederski et al.

(10) Patent No.: US 6,492,384 B1
(45) Date of Patent: Dec. 10, 2002

(54) IMIDAZO (4,5-C) PYRIDINE-4-ONE DERIVATIVES WITH FACTOR XA INHIBITING EFFECT

(75) Inventors: Werner Mederski, Erzhausen (DE); Horst Juraszyk, Seeheim (DE); Hanns Wurziger, Darmstadt (DE); Joachim Gante, deceased, late of Darmstadt (DE), by Helga Gante, legal representative; Dieter Dorsch, Ober-Ramstadt (DE); Hans-Peter Buchstaller, Weiterstadt (DE); Sabine Bernotat-Danielowski, Bad Nauheim (DE); Guido Melzer, Hofheim/Taunus (DE); Soheila Anzali, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/806,418

(22) PCT Filed: Sep. 9, 1999

(86) PCT No.: PCT/EP99/06655

§ 371 (c)(1),
(2), (4) Date: Dec. 13, 2001

(87) PCT Pub. No.: WO00/20416

PCT Pub. Date: Apr. 13, 2000

(30) Foreign Application Priority Data

Oct. 1, 1998 (DE) .......................... 198 45 153

(51) Int. Cl.[7] ..................... A61K 31/437; C07D 47/106
(52) U.S. Cl. ........................ 514/303; 546/118
(58) Field of Search ............................ 514/303; 546/118

(56) References Cited

U.S. PATENT DOCUMENTS

| | | |
|---|---|---|
| 5,389,642 A | 2/1995 | Dorsch et al. |
| 5,405,964 A | 4/1995 | Mederski et al. |
| 5,438,063 A | 8/1995 | Osswald et al. |
| 5,476,857 A | 12/1995 | Mederski et al. |
| 5,684,015 A | 11/1997 | Mederski et al. |
| 5,798,364 A * | 8/1998 | Mederski et al. ........... 514/303 |

FOREIGN PATENT DOCUMENTS

| | | | |
|---|---|---|---|
| CA | 2063926 A | | 9/1992 |
| CA | 2084736 A | | 6/1993 |
| CA | 2093290 A | | 10/1993 |
| CA | 2259573 A | | 1/1998 |
| DE | 0 505 893 A | * | 9/1992 |
| DE | 0 546 449 A | * | 6/1993 |
| DE | 0 564 960 A | * | 10/1993 |
| DE | 0 574 846 A | * | 12/1993 |
| DE | 0 595 151 A | * | 5/1994 |
| DE | 0 602 521 A | * | 6/1994 |
| DE | 0 628 556 A | * | 12/1994 |
| DE | 0 702 013 A | * | 3/1996 |
| WO | WO 98 01428 A | * | 1/1998 |

OTHER PUBLICATIONS

Mederski et al. Novel 4,5–dihydro–4–oxo–3H–imidazo,4, 5–clpyridines. Potent angiotension II receptor antagonists with high affinity for both the AT1 and AT2 subtypes. (1997). Eur. J. Med. Chem. 32(6), 479–491.*

Mederski et al. Non–peptide Angiotension II Receptor Antagonists: Synthesis and Biological Activity of a Series of Novel 4,5–Dihydro–4–oxo–3H–imidazo'4,5–clpyridine Derivatives. (1994). J. Med. Chem. 37(11), 1632–45.*

* cited by examiner

Primary Examiner—Joseph K. McKane
Assistant Examiner—Rebecca Anderson
(74) Attorney, Agent, or Firm—Millen, White, Zelano & Branigan, P.C.

(57) ABSTRACT

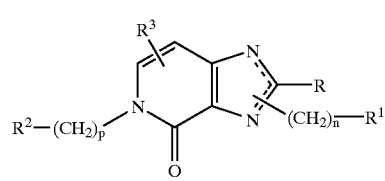

The invention relates to novel compounds of formula (I), wherein R, $R^1$, $R^2$, $R^3$, n and p have the meaning defined in claim 1. Compounds are inhibitors of clotting factor Xa and can be used for the prophylaxis and/or therapy of thromboembolic disorders.

7 Claims, No Drawings

IMIDAZO (4,5-C) PYRIDINE-4-ONE DERIVATIVES WITH FACTOR XA INHIBITING EFFECT

This is a 371 of International Application PCT/EP99/06655 with international filing date of Sep. 9, 1999, published in English.

The invention relates to compounds of the formula I

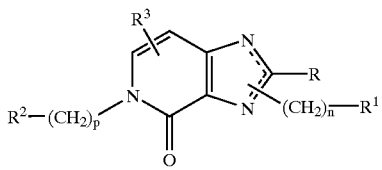

in which
R is H, unbranched or branched alkyl having 1–6 C atoms or cycloalkyl having 3–6 C atoms,
$R^1$ is Ar,
$R^2$ is Ar',
$R^3$ is H, R, $R^4$, Hal, CN, COOH, COOA or $CONH_2$,
Ar, Ar' are phenyl, naphthyl or biphenyl, in each case independently of one another unsubstituted or mono-, di- or trisubstituted by R, OH, Hal, CN, $NO_2$, $CF_3$, $NH_2$, NHR, $NR_2$, pyrrolidin-1-yl, piperidin-1-yl, benzyloxy, $SO_2NH_2$, $SO_2NHR$, $SO_2NR_2$, —CONHR, —$CONR_2$, —$(CH_2)_n$—$NH_2$—$(CH_2)_n$—NHR, —$(CH_2)_n$—$NR_2$, —O—$(CH_2)_n$—$NH_2$, —O—$(CH_2)_n$—NHR, —O—$(CH_2)_n$—$NR_2$, $R^4$ or together by —O—$(CH_2)_m$—O—, $R^4$ is —C(=NH)—$NH_2$ which is unsubstituted or monosubstituted by —COR, —COOR, —OH or by a conventional amino protective group or —NH—C(=NH)—$NH_2$, —C(=O)—N=C$(NH_2)_2$,

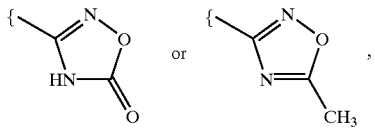

A is alkyl having 1–4 C atoms,
Hal is F, Cl, Br or I,
m is 1 or 2,
n is 0, 1, 2 or 3,
p is 0 or 1,
and their salts.

The invention also relates to the optically active forms, the racemates, the diastereomers and the hydrates and solvates, e.g. alcoholates, of these compounds.

The invention is based on the object of finding novel compounds having useful properties, in particular those which can be used for the production of medicaments.

It has been found that the compounds of the formula I and their salts have very useful pharmacological properties together with good tolerability. In particular, they show factor Xa-inhibiting properties and can therefore be employed for the control and prevention of thromboembolic disorders such as thrombosis, myocardial infarct, arteriosclerosis, inflammations, apoplexy, angina pectoris, restenosis after angioplasty and intermittent claudication.

The compounds of the formula I according to the invention can furthermore be inhibitors of the clotting factors factor VIIa, factor IXa and thrombin of the blood clotting cascade.

Aromatic amidine derivatives having antithrombotic action are disclosed, for example, in EP 0 540 051 B1. Cyclic guanidines for the treatment of thromboembolic disorders are described, for example, in WO 97/08165. Aromatic heterocycles having factor Xa-inhibitory activity are disclosed, for example, in WO 96/10022. Substituted N-[(aminoiminomethyl)phenylalkyl]azaheterocyclylamides as factor Xa inhibitors are described in WO 96/40679.

The antithrombotic and anticoagulating effect of the compounds according to the invention is attributed to the inhibiting action against the activated clotting protease, known under the name factor Xa, or to the inhibition of other activated serine proteases such as factor VIIa, factor IXa or thrombin.

Factor Xa is one of the proteases which is involved in the complex process of blood clotting. Factor Xa catalyses the conversion of prothrombin into thrombin. Thrombin cleaves fibrinogen into fibrin monomers which, after crosslinking, contribute elementarily to thrombus formation. Activation of thrombin can lead to the occurrence of thromboembolic disorders. Inhibition of thrombin, however, can inhibit the fibrin formation involved in thrombus formation. The inhibition of thrombin can be measured, for example, by the method of G. F. Cousins et al. in *Circulation* 1996, 94, 1705–1712.

Inhibition of factor Xa can thus prevent thrombin being formed. The compounds of the formula I according to the invention and their salts intervene in the blood clotting process by inhibition of factor Xa and thus inhibit the formation of thrombi.

The inhibition of factor Xa by the compounds according to the invention and the measurement of the [sic] anticoagulating and antithrombotic activity can be determined by customary in vitro or in vivo methods. A suitable procedure is described, for example, by J. Hauptmann et al. in *Thrombosis and Haemostatis* 1990, 63, 220–223.

The inhibition of factor Xa can be measured, for example, by the method of T. Hara et al. in *Thromb. Haemostas.* 1994, 71, 314–319.

After binding to tissue factor, the clotting factor VIIa initiates the intrinsic part of the clotting cascade and contributes to the activation of factor X to factor Xa. Inhibition of factor VIIa thus prevents the formation of factor Xa and thus subsequent thrombin formation. The inhibition of factor VIIa by the compounds according to the invention and the measurement of the [sic] anticoagulating and antithrombotic activity can be determined by customary in vitro or in vivo methods. A customary procedure for the measurement of the inhibition of factor VIIa is described, for example, by H. F. Ronning et al. in *Thrombosis Research* 1996, 84, 73–81.

The clotting factor IXa is generated in the intrinsic clotting cascade and is likewise involved in the activation of factor X to factor Xa. Inhibition of factor IXa can therefore prevent factor Xa being formed in another way. The inhibition of factor IXa by the compounds according to the invention and the measurement of the [sic] anticoagulating and antithrombotic activity can be determined by customary in vitro or in vivo methods. A suitable procedure is described, for example, by J. Chang et al. in *Journal of Biological Chemistry* 1998, 273, 12089–12094.

The compounds of the formula I can be employed as pharmaceutical active compounds in human and veterinary medicine, in particular for the control and prevention of thromboembolic disorders such as thrombosis, myocardial infarct, arteriosclerosis, inflammations, apoplexy, angina pectoris, restenosis after angioplasty and intermittent claudication.

The invention relates to the compounds of the formula I and their salts, and to a process for the preparation of compounds of the formula I according to claim 1 and their salts, characterized in that a) they are set free from one of their functional derivatives by treating with a solvolysing or hydrogenolysing agent, by
   i) liberating an amidino group from its oxadiazole derivative or oxazolidinone derivative by hydrogenolysis or solvolysis,
   ii) replacing a conventional amino protective group by hydrogen by treating with a solvolysing or hydrogenolysing agent or liberating an amino group protected by a conventional protective group, or
b) in a compound of the formula I, one or more radicals R, $R^1$, $R^2$ and/or $R^3$ are converted into one or more radicals R, $R^1$, $R^2$ and/or $R^3$, by, for example
   i) hydrolysing an ester group to a carboxyl group
   ii) reducing a nitro group
   iii) acylating an amino group
   iv) converting a cyano group into an amidino group and/or
c) a base or acid of the formula I is converted into one of its salts.

For all radicals which occur a number of times, it is a condition that their meanings are independent of one another.

Above and below, the radicals and parameters R, $R^1$, $R^2$, $R^3$ and n have the meanings indicated in the formula I, if not expressly stated otherwise.

R is alkyl, is unbranched (linear) or branched, and has 1 to 6, preferably 1, 2, 3, 4, 5 or 6, C atoms. R is preferably methyl, furthermore ethyl, propyl, isopropyl, butyl, isobutyl, sec-butyl or tert-butyl, in addition also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. R is also cycloalkyl and is preferably cyclopropyl, cyclobutyl, cyclopentyl, cyclohexyl or cycloheptyl. R is furthermore H.

A is alkyl having 1, 2, 3 or 4 C atoms and is preferably methyl, furthermore ethyl, propyl, isopropyl, butyl, isobutyl, sec-butyl or tert-butyl.

Hal is preferably F, Cl or Br, but also I.

Ar and Ar' are phenyl, benzodioxol-5-yl, naphthyl or biphenyl, in each case independently of one another unsubstituted or mono-, di- or trisubstituted by R, OH, OR, Hal, CN, $NO_2$, $CF_3$, $NH_2$, NHR, $NR_2$, pyrrolidin-1-yl, piperidin-1-yl, benzyloxy, $SO_2NH_2$, $SO_2NHA$, $SO_2NR_2$, phenylsulfonamido, —$(CH_2)_n$—$NH_2$, —$(CH_2)_n$—NHR, —$(CH_2)_n$—$NR_2$, —O—$(CH_2)_n$—$NH_2$, —O—$(CH_2)_n$—NHR, —O—$(CH_2)_n$—$NR_2$, —O—$(CH_2)_m$—O— or $R^4$, naphthyl or biphenyl monosubstituted by amidino being preferred. Preferred substituents for biphenyl are amidino, fluorine, $SO_2NH_2$ or $SO_2NHR$.

Ar and Ar' are phenyl, naphthyl or biphenyl, in each case independently of one another preferably unsubstituted, furthermore phenyl, naphthyl or biphenyl, preferably, for example, mono-, di- or trisubstituted by methyl, ethyl, propyl, isopropyl, butyl, cyclopentyl, cyclohexyl, fluorine, chlorine, bromine, iodine, hydroxyl, methoxy, ethoxy, propoxy, butyloxy, pentyloxy, hexyloxy, cyano, nitro, trifluoromethyl, amino, methylamino, ethylamino, dimethylamino, diethylamino, pyrrolidin-1-yl, piperidin-1-yl, benzyloxy, sulfonamido, methylsulfonamido, ethylsulfonamido, propylsulfonamido, butylsulfonamido, dimethylsulfonamido, phenylsulfonamido, aminomethyl, aminoethyl, N-methylaminomethyl, N-ethylaminomethyl, N,N-dimethylaminomethyl, aminomethyloxy, aminoethyloxy or $R^4$ and in addition benzodioxolyl.

Ar and Ar' are therefore, in each case independently of one another, very particularly preferably, for example, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-amidinophenyl, 7-amidino-2-naphthyl, 2'-amidinobiphenyl-3-yl, 3-fluoro-2'-sulfamoylbiphenyl-4-yl, 3-fluoro-2'-N-tert-butylsulfamoylbiphenyl-4-yl, 2'-sulfamoylbiphenyl-4-yl, 2'-N-tert-butylsulfamoylbiphenyl-4-yl, o-, m- or p-(pyrrolidin-1-yl)phenyl, o-, m- or p-(piperidin-1-yl)phenyl, o-, m- or p-{5-methyl[1,2,4]oxadiazol-3-yl)}phenyl, 7-{5-methyl[1,2,4]oxadiazol-3-yl)}naphth-2-yl, o-, m- or p-{5-oxo[1,2,4]oxadiazol-3-yl)}phenyl, 7-{5-oxo[1,2,4]oxadiazol-3-yl)}naphth-2-yl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

$R^3$ is preferably, for example, H, Hal, COOH, COOA or $CONH_2$.

$R^4$ is preferably, for example, unsubstituted —C(=NH)—$NH_2$, —NH—C(=NH)—$NH_2$, —C(=O)—N=C($NH_2)_2$, which can also be monosubstituted by OH,

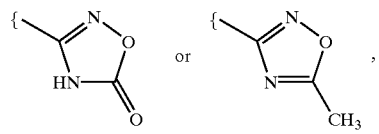

very particularly preferably unsubstituted —C(=NH)—$NH_2$ or

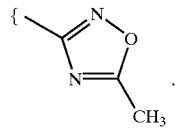

m is 1 or 2.

n is preferably 0 or 1, in addition also 2 or 3.

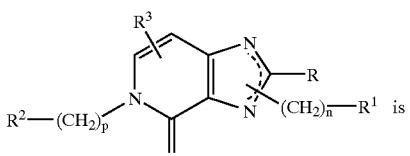

(IA)

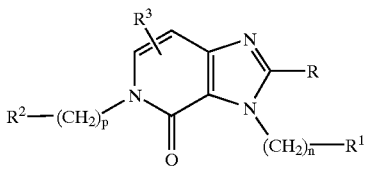

or (IB)

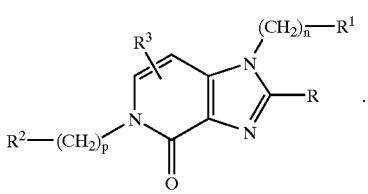

The compounds of the formula I can have one or more chiral centres and therefore occur in various stereoisomeric forms. The formula I includes all these forms.

Accordingly, the invention relates in particular to those compounds of the formula I in which at least one of the radicals mentioned has one of the preferred meanings indicated above. Some preferred groups of compounds can be expressed by the following subformulae Ia to Ii, which correspond to the formula I and in which the radicals not designated in greater detail have the meaning indicated in the formula I, but in which in Ia Ar is phenyl, naphthyl or biphenyl, which is monosubstituted by $R^4$;

in Ib Ar' is phenyl, naphthyl or biphenyl which is monosubstituted by $R^4$;

in Ic Ar, Ar' are phenyl, naphthyl or biphenyl, in each case independently of one another monosubstituted by $R^4$;

in Id Ar, Ar' are phenyl, naphthyl or biphenyl, in each case independently of one another monosubstituted by —$CONR_2$, $SO_2NH_2$ or $R^4$;

in Ie $R^3$ is H, R, Hal, COOH or COOA;

in If $R^4$ is —C(=NH)—$NH_2$ or

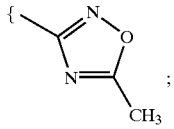

;

in Ig n is 1;

in Ih R is H, unbranched or branched alkyl having 1–6 C atoms or cycloalkyl having 3–6 C atoms, $R^1$ is Ar, $R^2$ is Ar'

$R^3$ is H, R, Hal, COOH or COOA,

Ar, Ar' are phenyl, naphthyl or biphenyl, in each case independently of one another monosubstituted by —$CONR_2$, $SO_2NH_2$ or $R^4$, $R^4$ is —C(=NH)—$NH_2$ or

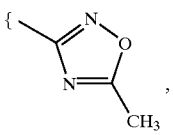

,

A is alkyl having 1–4 C atoms,

Hal is F, Cl, Br or I, m is 1 or 2, n is 0, 1, 2 or 3, in Ii R is H, unbranched or unbranched alkyl having 1–6 C atoms or cycloalkyl having 3–6 C atoms, $R^1$ is Ar, $R^2$ is Ar', $R^3$ is H, R, Hal, COCH or COCA, Ar, Ar' are phenyl, naphthyl or biphenyl, in each case independently of one another monosubstituted by $R^4$, $R^4$ is —C(=NH)—$NH_2$ or

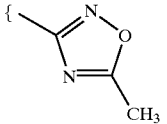

A is alkyl having 1–4 C atoms,

Hal is F, Cl, Br or I, m is 1 or 2, n is 0, 1, 2 or 3, p is 0 or 1.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the reactions mentioned. Use can also be made in this case of variants which are known per se, but not mentioned here in greater detail.

The starting substances can, if desired, also be formed in situ, such that they are not isolated from the reaction mixture, but immediately reacted further to give the compounds of the formula I.

Compounds of the formula I can preferably be obtained by setting compounds of the formula I free from one of their functional derivatives by treating with a solvolysing or hydrogenolysing agent.

Preferred starting substances for the solvolysis or hydrogenolysis are those which otherwise correspond to the formula I, but instead of one or more free amino and/or hydroxyl groups contain corresponding protected amino and/or hydroxyl groups, preferably those which, instead of an H atom which is bonded to an N atom, carry an amino protective group, in particular those which, instead of an HN group, carry an R'—N group in which R' is an amino protective group, and/or those which, instead of the H atom of a hydroxyl group, carry a hydroxyl protective group, e.g. those which correspond to the formula I, but instead of a group —COOH carry a group —COOR", in which R" is a hydroxyl protective group. Preferred starting substances are also the oxadiazole derivatives, which can be converted into the corresponding amidino compounds.

The amidino group can be liberated from its oxadiazole derivative, for example, by treating with hydrogen in the presence of a catalyst (e.g. Raney nickel). Suitable solvents are those indicated below, in particular alcohols such as methanol or ethanol, organic acids such as acetic acid or propionic acid, or mixtures thereof. As a rule, the hydrogenolysis is carried out at temperatures between approximately 0 and 100° and pressures between approximately 1 and 200 bar, preferably at 20–30° (room temperature) and 1–10 bar.

The oxadiazole group is introduced, for example, by reaction of the cyano compounds with hydroxylamine and reaction with phosgene, dialkyl carbonate, chloroformic acid esters, N,N'-carbonyldiimidazole or acetic anhydride.

A number of—identical or different—protected amino and/or hydroxyl groups can also be present in the molecule of the starting substance. If the protective groups present are different from one another, in many cases they can be removed selectively.

The expression "amino protective group" is generally known and relates to groups which are suitable for protecting (for blocking) an amino group from chemical reactions, but which are easily removable after the desired chemical reaction has been carried out at other positions in the molecule. Typical groups of this type are, in particular, unsubstituted or substituted acyl, aryl, aralkoxymethyl or aralkyl groups. Since the amino protective groups are removed after the desired reaction (or reaction sequence), their nature and size is otherwise not critical; however, those having 1–20, in particular 1–8, C atoms are preferred. The expression "acyl group" is to be interpreted in the widest sense in connection with the present process. It includes acyl groups derived from aliphatic, araliphatic, aromatic or heterocyclic carboxylic acids or sulfonic acids and, in particular, alkoxycarbonyl, aryloxycarbonyl and especially aralkoxycarbonyl groups. Examples of acyl groups of this type are alkanoyl such as acetyl, propionyl, butyryl; aralkanoyl such as phenylacetyl; aroyl such as benzoyl or toluyl; aryloxyalkanoyl such as POA; alkoxycarbonyl such as methoxycarbonyl, ethoxycarbonyl, 2,2,2-trichloroethoxycarbonyl, BOC (tert-butyloxycarbonyl), 2-iodoethoxycarbonyl; aralkyloxycarbonyl such as CBZ ("carbobenzoxy"), 4-methoxybenzyloxycarbonyl, FMOC; arylsulfonyl such as Mtr. Preferred amino protective groups are BOC and Mtr, in addition CBZ, Fmoc, benzyl and acetyl.

The expression "hydroxyl protective group" is likewise generally known and relates to groups which are suitable for protecting a hydroxyl group from chemical reactions, but which are easily removable after the desired chemical reaction has been carried out at other positions in the molecule. Typical groups of this type are the abovementioned unsubstituted or substituted aryl, aralkyl or acyl groups, in addition also alkyl groups. The nature and size of the hydroxyl protective groups is not critical, since they are removed again after the desired chemical reaction or reaction sequence; groups having 1–20, in particular 1–10, C atoms are preferred. Examples of hydroxyl protective groups are, inter alia, benzyl, 4-methoxybenzyl, p-nitrobenzoyl [sic], p-toluenesulfonyl, tert-butyl and acetyl, benzyl and tert-butyl being particularly preferred.

The liberation of the compounds of the formula I from their functional derivatives is carried out—depending on the protective group used—for example using strong acids, expediently using TFA or perchloric acid, but also using other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent is possible, but not always necessary. Suitable inert solvents are preferably organic, for example carboxylic acids such as acetic acid, ethers such as tetrahydrofuran or dioxane, amides such as DMF, halogenated hydrocarbons such as dichloromethane, in addition also alcohols such as methanol, ethanol or isopropanol, and also water. Mixtures of the abovementioned solvents are additionally suitable. TFA is preferably used in an excess without addition of a further solvent, perchloric acid in the form of a mixture of acetic acid and 70% perchloric acid in the ratio 9:1. The reaction temperatures for the cleavage are expediently between approximately 0 and approximately 50°; the reaction is preferably carried out between 15 and 30° (room temperature).

The groups BOC, OBut and Mtr can be removed, for example, preferably using TFA in dichloromethane or using approximately 3 to 5N HCl in dioxane at 15–30°; the FMOC group using approximately 5 to 50% solution of dimethylamine, diethylamine or piperidine in DMF at 15–30°.

Hydrogenolytically removable protective groups (e.g. CBZ, benzyl or the liberation of the amidino group from its oxadiazole derivative)) can be removed for example by treating with hydrogen in the presence of a catalyst (e.g. of a noble metal catalyst such as palladium, expediently on a support such as carbon) [sic]. Suitable solvents here are those indicated above, in particular, for example, alcohols such as methanol or ethanol or amides such as DMF. As a rule, the hydrogenolysis takes place at temperatures between approximately 0 and 100° and pressures between approximately 1 and 200 bar, preferably at 20–30° and 1–10 bar. Hydrogenolysis of the CBZ group takes place readily, for example, on 5 to 10% Pd/C in methanol or using ammomium [sic] formate (instead of hydrogen) on Pd/C in methanol/DMF at 20–30°.

Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, trifluoromethylbenzene, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide, N-methylpyrrolidone (NMP) or dimethylformamide (DMF); nitrites such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate or mixtures of the solvents mentioned.

The biphenyl-$SO_2NH_2$ group is preferably employed in the form of its tert-butyl derivative. The tert-butyl group is removed, for example, using TFA with or without addition of an inert solvent, preferably with addition of a small amount of anisole (1% by volume).

The cyano group is converted into an amidino group by reaction with, for example, hydroxylamine and subsequent reduction of the N-hydroxyamidine with hydrogen in the presence of a catalyst such as, for example, Pd/C. For the preparation of an amidine of the formula I (e.g. Ar=phenyl monosubstituted by C($=$NH)—$NH_2$), ammonia can also be added to a nitrile. The addition is preferably carried out in a number of stages in a manner known per se by a) converting the nitrile using H₂S into a thioamide, which is converted using an alkylating agent, e.g. CH₃I, into the corresponding S-alkyl imidothioester, which for its part is reacted with NH₃ to give the amidine, b) converting the nitrile into the corresponding imido ester using an alcohol, e.g. ethanol in the presence of HCl, and treating this with ammonia, or c) reacting the nitrile with lithium bis(trimethylsilyl)amide and then hydrolysing the product.

The radicals $R^2$ and —$(CH_2)_n$—$R^1$ are introduced into the dihydroimidazo[4,5-c]pyridin-4-one system by customary alkylation methods. Thus it is possible, for example, to react a compound of the formula II

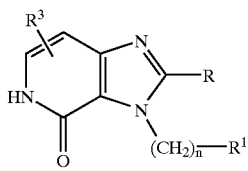

II in which R has the meaning indicated in claim 1 and $R^1$ and $R^3$ are each a radical of the type which cannot be alkylated, such as, for example, for $R^1$ a phenyl or naphthyl radical substituted by

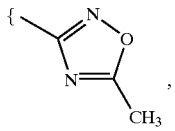

with a compound of the formula III

III in which L is Cl, Br, I or a free or reactively [sic] functionally modified OH group, and p is 1, and by this process compounds of the formula (IA) are obtained.

L is preferably Cl, Br, I or a reactively [sic] modified OH group such as, for example, an activated ester, an imidazolide or alkylsulfonyloxy having 1–6 C atoms (preferably methylsulfonyloxy) or arylsulfonyloxy having 6–10 C atoms (preferably phenyl- or p-tolylsulfonyloxy).

Suitable solvents are those mentioned above. The reaction is carried out in the presence of an acid-binding agent, preferably of an alkali metal or alkaline earth metal hydroxide, carbonate or bicarbonate or of another salt of a weak acid of the alkali metals or alkaline earth metals, preferably of potassium, sodium, calcium or caesium. The addition of an organic base such as triethylamine, dimethylaniline, pyridine or quinoline can also be favourable. Depending on the conditions used, the reaction time is between a few minutes and 14 days, and the reaction temperature is between approximately 0° and 150°, normally between 20° and 130°.

In compounds where p=0, $R^2$ is introduced via a boronic acid derivative.

Analogously, $R^2$—$(CH_2)_p$—, in which p=1, can also firstly be introduced into the dihydroimidazo[4,5-c]pyridin-4-one system and then a compound of the formula IV

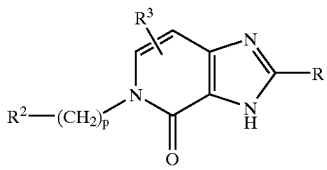

IV in which p=1 and R has the meaning indicated in claim 1 and $R^2$ and $R^3$ are each a radical of the type which cannot be alkylated, can be reacted with a compound of the formula V

$R^1$—$(CH_2)_n$—L     V.

In the compounds of the formula V, $R^1$ is a radical which cannot be alkylated, such as, for example, a phenyl radical substituted by 5-methyl-[1,2,4]oxadiazol-3-yl and L has the meaning as in the compounds of the formula III. Compounds of the formula (IA) and/or (IB) are obtained by this process.

In addition, it is possible to convert a compound of the formula I into another compound of the formula I by converting one or more radicals R, $R^1$, $R^2$ and/or $R^3$ into one or more radicals R, $R^1$, $R^2$ and/or $R^3$, e.g. by acylating an amino group or reducing nitro groups (for example by hydrogenation on Raney nickel or Pd-carbon in an inert solvent such as methanol or ethanol) to amino groups.

Esters can be hydrolysed, for example, using acetic acid or using NaOH or KOH in water, water-THF or water-dioxane at temperatures between 0 and 100°.

In addition, free amino groups can be acylated in a customary manner using an acid chloride or anhydride or alkylated using an unsubstituted or substituted alkyl halide, expediently in an inert solvent such as dichloromethane or THF and/or in the presence of a base such as triethylamine or. pyridine at temperatures between −60 and +30°.

A base of the formula I can be converted into the associated acid addition salt using an acid, for example by reaction of equivalent amounts of the base and of the acid in an inert solvent such as ethanol and subsequent evaporation. Acids suitable for this reaction are in particular those which yield physiologically acceptable salts. Thus, inorganic acids can be used, e.g. sulfuric acid, nitric acid, hydrohalic acids such as hydrochloric acid or hydrobromic acid, phosphoric acids such as orthophosphoric acid, sulfamic acid, in addition organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, and laurylsulfonic acid. Salts with physiologically unacceptable acids, e.g. picrates., can be used for the isolation and/or purification of the compounds of the formula I.

On the other hand, compounds of the formula I can be converted into the corresponding metal salts, in particular alkali metal or alkaline earth metal salts, or into the corresponding ammonium salts using bases (e.g. sodium or potassium hydroxide or carbonate). Physiologically acceptable organic bases, e.g. ethanolamine can also be used.

Compounds of the formula I according to the invention can be chiral on account of their molecular structure and can accordingly occur in various enantiomeric forms. They can therefore be present in racemic or in optically active form.

Since the pharmaceutical activity of the racemates or of the stereoisomers of the compounds according to the invention can differ, it can be desirable to use the enantiomers. In these cases, the final product or else even the intermediates can be separated into enantiomeric compounds by chemical or physical measures known to the person skilled in the art, or even employed as such in the synthesis.

In the case of racemic amines, diastereomers are formed from the mixture by reaction with an optically active resolving agent. Suitable resolving agents are, for example, optically active acids, such as the R and S forms of tartaric acid, diacetyltartaric acid, dibenzoyltartaric acid, mandelic acid, malic acid, lactic acid, suitably N-protected amino acids (e.g. N-benzoylproline or N-benzenesulfonylproline) or the various optically active camphorsulfonic acids. Chromatographic resolution of enantiomers with the aid of an optically active resolving agent (e.g. dinitrobenzoylphenylglycine, cellulose triacetate or other derivatives of carbohydrates or chiral derivatized methacrylate polymers attached to silica gel) is also advantageous. Suitable eluents for this are aqueous or alcoholic solvent mixtures such as, for example, hexane/isopropanol/acetonitrile, e.g. in the ratio 82:15:3.

The invention further relates to the use of the compounds of the formula I and/or their physiologically acceptable salts for the production of pharmaceutical preparations, in particular in a non-chemical manner. In this connection, they can be brought into a suitable dose form together with at least one solid, liquid and/or semi-liquid excipient or auxiliary and, if appropriate, in combination with one or more other active compounds.

The invention further relates to pharmaceutical preparations comprising at least one compound of the formula I and/or one of its physiologically acceptable salts.

These preparations can be used as medicaments in human or veterinary medicine. Possible excipients are organic or inorganic substances which are suitable for enteral (e.g. oral) or parenteral administration or topical application and do not react with the novel compounds, for example water, vegetable oils, benzyl alcohols, alkylene glycols, polyethylene glycols, glycerol triacetate, gelatin, carbohydrates such as lactose or starch, magnesium stearate, talc, petroleum jelly. Tablets, pills, coated tablets, capsules, powders, granules, syrups, juices or drops, in particular, are used for oral administration, suppositories are used for rectal administration, solutions, preferably oily or aqueous solutions, in addition to suspensions, emulsions or implants, are used for parenteral administration, and ointments, creams or powders are used for topical application. The novel compounds can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or [lacuna] more further active compounds, e.g. one or more vitamins.

The compounds of the formula I and their physiologically acceptable salts can be used in the control and prevention of thromboembolic disorders such as thrombosis, myocardial infarct, arteriosclerosis, inflammations, apoplexy, angina pectoris, restenosis after angioplasty and intermittent claudication.

In this connection, as a rule the substances according to the invention are preferably administered in doses of between approximately 1 and 500 mg, in particular between 5 and 100 mg, per dose unit. The daily dose is preferably between approximately 0.02 and 10 mg/kg of body weight. The specific dose for each patient depends on all sorts of factors, however, for example on the efficacy of the specific compound employed, on the age, body weight, general state of health, sex, on the diet, on the time and route of administration, and on the excretion rate, pharmaceutical combination and severity of the particular disorder to which the therapy applies. Oral administration is preferred.

Above and below, all temperatures are indicated in ° C. In the following examples, "customary working up" means: water is added, if necessary, the mixture is adjusted, if necessary, depending on the constitution of the final product, to a pH of between 2 and 10 and extracted with ethyl acetate or dichloromethane, the extract is separated off, the organic phase is dried over sodium sulfate and evaporated, and the residue is purified by chromatography on silica gel and/or by crystallization. $R_f$ values on silica gel; eluent:ethyl acetate/methanol 9:1.

Mass spectrometry (MS): EI (electron impact ionization) $M^+$ FAB (fast atom bombardment) $(M+H)^+$

EXAMPLE 1

140 ml of isobutyric acid and 250 ml of fuming hydrochloric acid are added to 50.0 g of 3,4-diamino-2-chloropyridine. The reaction mixture is heated under reflux for 7 days. It is poured into ice water, the deposited precipitate is separated off and 2-isopropyl-3,5-dihydroimidazo [4,5-c]pyridin-4-one ("AB"), m.p. 310–311° (decomposition), EI 177 is obtained

"AB"

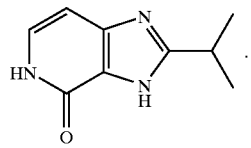

A mixture of "AB" and 4-chloro-2-isopropyl-3H-imidazo [4,5-c]pyridine is found in the mother liquor. A solution of 0.877 g of "AB" and 0.691 g of potassium carbonate in 30 ml of DMF is stirred at room temperature for 30 minutes. 1.5 g of 3-(7-bromomethylnaphthalen-2-yl)-5-methyl[1,2,4] oxadiazole (m.p. 149–150°) are added and the mixture is stirred for 16 hours and worked up in the customary manner. After chromatography on silica gel, in addition to the two regioisomeric dialkylation products, the compound 2-isopropyl-3-[7-(5-methyl[1,2,4]oxadiazol-3-yl)naphth-2-ylmethyl]-5H-imidazo[4,5-c]pyridin-4-one ("BB"), m.p. 214–215° EI 399 is obtained

"BB"

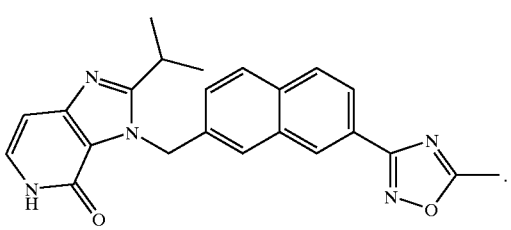

An alternative process leads to "BB" as follows (analogously to Mederski et al., J. Med. Chem. 1994, 1632 ff): reaction of 3,4-diamino-2-chloropyridine with isobutyric anhydride to give N-(4-amino-2-chloropyridin-3-yl) isobutyramide. The subsequent reaction with 3-(7-bromomethylnaphthalen-2-yl)-5-methyl-[1,2,4]oxadiazole leads to a mixture of 4-chloro-2-isopropyl-3-[7-(5-methyl [1,2,4]oxadiazol-3-yl)naphth-2-ylmethyl]-3H-imidazo[4,5-c]pyridine and N-(4-amino-2-chloropyridin-3-yl)-N-[7-(5-methyl[1,2,4]oxadiazol-3-yl)naphth-2-ylmethyl] isobutyramide. Both compounds are reacted to give "BB".

62 mg of potassium tertiary-butoxide are added to a solution of 0.2 g of "BB" in 10 ml of DMF and the mixture is stirred for 30 minutes. 0.140 g of 3-(3-bromomethylphenyl)-5-methyl[1,2,4]oxadiazole is then added and the mixture is stirred for a further 2 hours. After customary working up, the compound 2-isopropyl-3-[7-(5-methyl[1,2,4]oxadiazol-3-yl)naphth-2-ylmethyl]-5-[3-(5-methyl[1,2,4]oxadiazol-3-yl)benzyl]-3,5-dihydroimidazo[4,5-c]pyridin-4-one ("BC1"), m.p. 108–109°, EI 571 is obtained (analogously to WO 97/21437, pp. 44–45), a mixture of 2-isopropyl-3-tert-butyloxycarbonyl-5H-imidazo[4,5-c] pyridin-4-one and 2-isopropyl-1-tert-butyloxycarbonyl-5H-imidazo[4,5-c]pyridin-4-one is obtained.

The mixture of the two compounds is reacted with 3-(3-bromomethylphenyl)-5-methyl[1,2,4]oxadiazole analogously to Example 1 and a mixture of the two compounds 2-isopropyl-3-tert-butyloxycarbonyl-5-[3-(5-methyl[1,2,4] oxadiazol-3-yl)benzyl]-3,5-dihydroimidazo-[4,5-c] pyridin-4-one and
2-isopropyl-1-tert-butyloxycarbonyl-5-[3-(5-methyl[1,2,4] oxadiazol-3-yl)benzyl]-1,5-dihydroimidazo[4,5-c] pyridin-4-one is obtained.

After removal of the BOC protective groups using TFA in dioxane and customary working up, the mixture is reacted with 3-(7-bromomethylnaphthalen-2-yl)-5-methyl[1,2,4] oxadiazole analogously to Example 1. After customary working up, a mixture of regioisomeric products is obtained, from which "BC1" is separated off by chromatography.

"BC1"

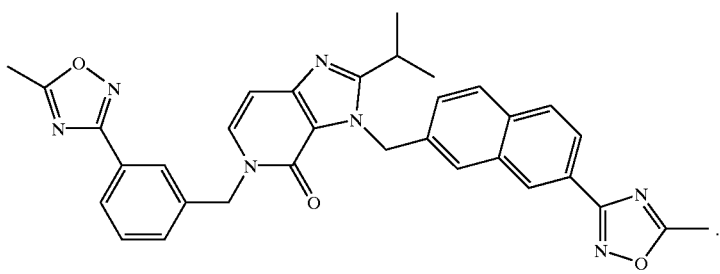

Analogously, by reaction of "BB" with
3-(7-bromomethylnaphthalen-2-yl)-5-methyl[1,2,4] oxadiazole,
3-(4-bromomethylphenyl)-5-methyl[1,2,4]oxadiazole,
3-(2-bromomethylphenyl)-5-methyl[1,2,4]oxadiazole, benzyl bromide,
3-dimethylaminocarbonylbenzyl bromide,
3'-(N-tert-butylsulfonamido)biphenyl-3-ylmethyl bromide, the compounds below are obtained
2-isopropyl-3-[7-(5-methyl[1,2,4]oxadiazol-3-yl)naphth-2-ylmethyl]-5-[7-(5-methyl[1,2,4]oxadiazol-3-yl)naphth-2-ylmethyl]-3,5-dihydroimidazo[4,5-c]pyridin-4-one ("BC2"), m.p. 201–202°;
2-isopropyl-3-[7-(5-methyl[1,2,4]oxadiazol-3-yl)naphth-2-ylmethyl]-5-[4-(5-methyl[1,2,4]oxadiazol-3-yl)benzyl]-3,5-dihydroimidazo[4,5-c]pyridin-4-one ("BC3"), m.p. 172–173°;
2-isopropyl-3-[7-(5-methyl[1,2,4]oxadiazol-3-yl)naphth-2-ylmethyl]-5-[2-(5-methyl[1,2,4]oxadiazol-3-yl)benzyl]-3,5-dihydroimidazo[4,5-c]pyridin-4-one ("BC4"), m.p. 149–150°;
2-isopropyl-3-[7-(5-methyl[1,2,4]oxadiazol-3-yl)naphth-2-ylmethyl]-5-benzyl-5H-imidazo[4,5-c]pyridin-4-one ("BC5"), m.p. 112–113°;
2-isopropyl-3-[7-(5-methyl[1,2,4]oxadiazol-3-yl)naphth-2-ylmethyl]-5-(3-dimethylaminocarbonylbenzyl)-5H-imidazo[4,5-c]pyridin-4-one ("BC6"),
2-isopropyl-3-[7-(5-methyl[1,2,4]oxadiazol-3-yl)naphth-2-ylmethyl]-5-[3'-(N-tert-butylsulfonamido)biphenyl-3-ylmethyl]-5H-imidazo[4,5-c]pyridin-4-one ("BC7"), FAB 639.

EXAMPLE 2

Alternative Process for the Preparation of "BC1"

By reaction of 3,4-diamino-2-chloropyridine with isobutyric acid and then with di(tert-butyloxy)anhydride

EXAMPLE 3

A solution of 0.2 g of "BC1" in 20 ml of methanol is treated with 100 mg of Raney nickel and a drop of acetic acid and hydrogenated at room temperature for 8 hours. The catalyst is filtered off, the solvent is removed and the compound
2-isopropyl-3-(7-amidinonaphth-2-ylmethyl)-5-(3-amidinobenzyl)-3,5-dihydroimidazo[4,5-c]pyridin-4-one, m.p. >300° (decomposition), FAB 492, is obtained.
Analogously, starting from "BC2", "BC3", "BC4", "BC5", "BC6" and "BC7", the compounds below are obtained
2-isopropyl-3-(7-amidinonaphth-2-ylmethyl)-5-(7-amidinonaphth-2-ylmethyl)-3,5-dihydroimidazo[4,5-c] pyridin-4-one, m.p. >300°, EI 166;
2-isopropyl-3-(7-amidinonaphth-2-ylmethyl)-5-(4-amidinobenzyl)-3,5-dihydroimidazo[4,5-c]pyridin-4-one, m.p. 208–209° (decomposition), FAB 492;
2-isopropyl-3-(7-amidinonaphth-2-ylmethyl)-5-(2-amidinobenzyl)-3,5-dihydroimidazo[4,5-c]pyridin-4-one, m.p. >300°, FAB 492;
2-isopropyl-3-[7-amidinonaphth-2-ylmethyl]-5-benzyl-5H-imidazo[4,5-c]pyridin-4-one, m.p. 206–207 (decomposition), FAB 450;
2-isopropyl-3-[7-amidinonaphth-2-ylmethyl]-5-(3-dimethylaminocarbonylbenzyl)-5H-imidazo[4,5-c] pyridin-4-one,
2-isopropyl-3-[7-amidinonaphth-2-ylmethyl]-5-[3'-(N-tert-butylsulfonamido)biphenyl-3-ylmethyl]-5H-imidazo[4,5-c]pyridin-4-one ("DF").
Analogously, 3-(7-amidinonaphth-2-ylmethyl)-5-(3-amidinobenzyl)-3,5-dihydroimidazo[4,5-c]pyridin-4-one, m.p. >300°, FAB 450, is obtained.

EXAMPLE 4

Analogously to Example 1, the compound 2-isopropyl-3-[3-(5-methyl[1,2,4]oxadiazol-3-yl)benzyl]-5H-imidazo[4, 5-c]pyridin-4-one ("CA") is obtained by reaction of "AB" with 3-(3-bromomethylphenyl)-5-methyl[1,2,4]oxadiazole.

By reaction of "CA" with
3-(3-bromomethylphenyl)-5-methyl[1,2,4]oxadiazole,
3-(7-bromomethylnaphthalen-2-yl)-5-methyl[1,2,4]oxadiazole,
3-(4-bromomethylphenyl)-5-methyl[1,2,4]oxadiazole,
3-(2-bromomethylphenyl)-5-methyl[1,2,4]oxadiazole,
the dialkylated imidazo derivatives are obtained, which are converted into the compounds below by hydrogenation analogously to Example 3
2-isopropyl-3-(3-amidinobenzyl)-5-(3-amidinobenzyl)-3,5-dihydroimidazo[4,5-c]pyridin-4-one,
2-isopropyl-3-(3-amidinobenzyl)-5-(7-amidinonaphth-2-ylmethyl)-3,5-dihydroimidazo[4,5-c]pyridin-4-one,
2-isopropyl-3-(3-amidinobenzyl)-5-(4-amidinobenzyl)-3,5-dihydroimidazo[4,5-c]pyridin-4-one,
2-isopropyl-3-(3-amidinobenzyl)-5-(2-amidinobenzyl)-3,5-dihydroimidazo[4,5-c]pyridin-4-one.

EXAMPLE 5

By reaction of 3,4-diamino-2-chloropyridine analogously to Example 1 with the carboxylic acids below
propionic acid,
cyclopropylcarboxylic acid,
subsequent alkylation of the resulting imidazo derivatives analogously to Examples 1 and 4 and hydrogenation analogously to Example 3, the compounds below are obtained
2-ethyl-3-(7-amidinonaphth-2-ylmethyl)-5-(3-amidinobenzyl)-3,5-dihydroimidazo[4,5-c]pyridin-4-one, m.p. 145°, FAB 478;
2-ethyl-3-(7-amidinonaphth-2-ylmethyl)-5-(7-amidinonaphth-2-ylmethyl)-3,5-dihydroimidazo[4,5-c]pyridin-4-one,
2-ethyl-3-(7-amidinonaphth-2-ylmethyl)-5-(4-amidinobenzyl)-3,5-dihydroimidazo[4,5-c]pyridin-4-one,
2-ethyl-3-(7-amidinonaphth-2-ylmethyl)-5-(2-amidinobenzyl)-3,5-dihydroimidazo[4,5-c]pyridin-4-one,
2-ethyl-3-(3-amidinobenzyl)-5-(3-amidinobenzyl)-3,5-dihydroimidazo[4,5-c]pyridin-4-one,
2-ethyl-3-(3-amidinobenzyl)-5-(7-amidinonaphth-2-ylmethyl)-3,5-dihydroimidazo[4,5-c]pyridin-4-one,
2-ethyl-3-(3-amidinobenzyl)-5-(4-amidinobenzyl)-3,5-dihydroimidazo[4,5-c]pyridin-4-one,
2-ethyl-3-(3-amidinobenzyl)-5-(2-amidinobenzyl)-3,5-dihydroimidazo[4,5-c]pyridin-4-one,
2-cyclopropyl-3-(7-amidinonaphth-2-ylmethyl)-5-(3-amidinobenzyl)-3,5-dihydroimidazo[4,5-c]pyridin-4-one,
2-cyclopropyl-3-(7-amidinonaphth-2-ylmethyl)-5-(7-amidinonaphth-2-ylmethyl)-3,5-dihydroimidazo[4,5-c]pyridin-4-one,
2-cyclopropyl-3-(7-amidinonaphth-2-ylmethyl)-5-(4-amidinobenzyl)-3,5-dihydroimidazo[4,5-c]pyridin-4-one,
2-cyclopropyl-3-(7-amidinonaphth-2-ylmethyl)-5-(2-amidinobenzyl)-3,5-dihydroimidazo[4,5-c]pyridin-4-one,
2-cyclopropyl-3-(3-amidinobenzyl)-5-(3-amidinobenzyl)-3,5-dihydroimidazo[4,5-c]pyridin-4-one,
2-cyclopropyl-3-(3-amidinobenzyl)-5-(7-amidinonaphth-2-ylmethyl)-3,5-dihydroimidazo[4,5-c]pyridin-4-one,
2-cyclopropyl-3-(3-amidinobenzyl)-5-(4-amidinobenzyl)-3,5-dihydroimidazo[4,5-c]pyridin-4-one,
2-cyclopropyl-3-(3-amidinobenzyl)-5-(2-amidinobenzyl)-3,5-dihydroimidazo[4,5-c]pyridin-4-one.
Analogously, the compounds
2-isobutyl-3-(7-amidinonaphth-2-ylmethyl)-5-(3-amidinobenzyl)-3,5-dihydroimidazo[4,5-c]pyridin-4-one, m.p. 69–70°, FAB 506;
2-methyl-3-(7-amidinonaphth-2-ylmethyl)-5-(3-amidinobenzyl)-3,5-dihydroimidazo[4,5-c]pyridin-4-one, m.p. 171–172°, FAB 464;
2-butyl-3-(7-amidinonaphth-2-ylmethyl)-5-(3-amidinobenzyl)-3,5-dihydroimidazo[4,5-c]pyridin-4-one, m.p. 190–191°, FAB 506, are obtained.

EXAMPLE 6

By reaction of 3,4-diamino-2-chloro-5-methoxycarbonylpyridine (m.p. 181–184°) with isobutyric acid analogously to Example 1, 2-isopropyl-3,5-dihydro-7-carboxyimidazo[4,5-c]pyridin-4-one is obtained. The carboxylic acid is reacted by customary methods to give 2-isopropyl-3,5-dihydro-7-methoxycarbonylimidazo-[4,5-c]pyridin-4-one and then alkylated analogously to Examples 1 and 4 and hydrogenated analogously to Example 3. In this process, the carboxylic acid derivatives below are obtained
7-carboxy-2-isopropyl-3-(7-amidinonaphth-2-ylmethyl)-5-(3-amidinobenzyl)-3,5-dihydroimidazo-[4,5-c]pyridin-4-one,
7-carboxy-2-isopropyl-3-(7-amidinonaphth-2-ylmethyl)-5-(7-amidinonaphth-2-ylmethyl)-3,5-dihydroimidazo[4,5-c]pyridin-4-one,
7-carboxy-2-isopropyl-3-(7-amidinonaphth-2-ylmethyl)-5-(4-amidinobenzyl)-3,5-dihydroimidazo-[4,5-c]pyridin-4-one,
7-carboxy-2-isopropyl-3-(7-amidinonaphth-2-ylmethyl)-5-(2-amidinobenzyl)-3,5-dihydroimidazo-[4,5-c]pyridin-4-one.
7-carboxy-2-isopropyl-3-(3-amidinobenzyl)-5-(3-amidinobenzyl)-3,5-dihydroimidazo[4,5-c]pyridin-4-one,
7-carboxy-2-isopropyl-3-(3-amidinobenzyl)-5-(7-amidinonaphth-2-ylmethyl)-3,5-dihydroimidazo[4,5-c]pyridin-4-one,
7-carboxy-2-isopropyl-3-(3-amidinobenzyl)-5-(4-amidinobenzyl)-3,5-dihydroimidazo[4,5-c]pyridin-4-one,
7-carboxy-2-isopropyl-3-(3-amidinobenzyl)-5-(2-amidinobenzyl)-3,5-dihydroimidazo[4,5-c]pyridin-4-one.

EXAMPLE 7

By reaction of 3,4-diamino-2-chloro-5-bromopyridine (m.p. 206–208°) with isobutyric acid analogously to Example 1, 2-isopropyl-3,5-dihydro-7-bromoimidazo-[4,5-c]pyridin-4-one is obtained. This is then alkylated analogously to Examples 1 and 4 and hydrogenated analogously to Example 3. In this process, the compounds below are obtained
7-bromo-2-isopropyl-3-(7-amidinonaphth-2-ylmethyl)-5-(3-amidinobenzyl)-3,5-dihydroimidazo-[4,5-c]pyridin-4-one,
7-bromo-2-isopropyl-3-(7-amidinonaphth-2-ylmethyl)-5-(7-amidinonaphth-2-ylmethyl)-3,5-dihydroimidazo[4,5-c]pyridin-4-one,
7-bromo-2-isopropyl-3-(7-amidinonaphth-2-ylmethyl)-5-(4-amidinobenzyl)-3,5-dihydroimidazo-[4,5-c]pyridin-4-one,
7-bromo-2-isopropyl-3-(7-amidinonaphth-2-ylmethyl)-5-(2-amidinobenzyl)-3,5-dihydroimidazo-[4,5-c]pyridin-4-one.
7-bromo-2-isopropyl-3-(3-amidinobenzyl)-5-(3-amidinobenzyl)-3,5-dihydroimidazo[4,5-c]pyridin-4-one,
7-bromo-2-isopropyl-3-(3-amidinobenzyl)-5-(7-amidinonaphth-2-ylmethyl)-3,5-dihydroimidazo-[4,5-c]pyridin-4-one,
7-bromo-2-isopropyl-3-(3-amidinobenzyl)-5-(4-amidinobenzyl)-3,5-dihydroimidazo[4,5-c]pyridin-4-one, 7-bromo-2-isopropyl-3-(3-amidinobenzyl)-5-(2-amidinobenzyl)-3,5-dihydroimidazo[4,5-c]pyridin-4-one.

EXAMPLE 8

By reaction of 2-isopropyl-3,5-dihydro-7-bromoimidazo-[4,5-c]pyridin-4-one with CuCN in DMF by customary methods (Ellefson et al., J. Med. Chem. 1976, 19), 2-isopropyl-3,5-dihydro-7-cyanoimidazo[4,5-c]pyridin-4-one is obtained. This is then hydrolysed and alkylated analogously to Examples 1 and 4 and hydrogenated analogously to Example 3. In this process, the carboxylic acid derivatives listed under Example 6 are obtained.

EXAMPLE 9

Analogously to Example 1, the compound 2-isopropyl-3-[3'-(5-methyl[1,2,4]oxadiazol-3-yl)biphenyl-3-ylmethyl]-5H-imidazo[4,5-c]pyridin-4-one ("CD") is obtained by reaction of "AB" with 3-(3-bromomethylbiphenyl-3'-yl)-5-methyl[1,2,4]oxadiazole, customary working up and chromatography.

By reaction of "CD" with
3-(3-bromomethylphenyl)-5-methyl[1,2,4]oxadiazole,
3-(3-bromomethylbiphenyl-3'-yl)-5-methyl[1,2,4]oxadiazole,
and subsequent hydrogenation, the compounds below are obtained
2-isopropyl-3-[3'-amidinobiphenyl-3-ylmethyl]-5-(3-amidinobenzyl)-5H-imidazo[4,5-c]pyridin-4-one and
2-isopropyl-3-[3'-amidinobiphenyl-3-ylmethyl]-5-[3'-amidinobiphenyl-3-ylmethyl]-5H-imidazo[4,5-c]pyridin-4-one.
Analogously, the compound
2-isopropyl-3-[4'-amidinobiphenyl-3-ylmethyl]-5-benzyl-5H-imidazo[4,5-c]pyridin-4-one, m.p. >300°, EI 475, is obtained.

EXAMPLE 10

Starting from "DF", by removal of the tert-butyl group in TFA, by customary methods the compound
2-isopropyl-3-[7-amidinonaphth-2-ylmethyl]-3-(3'-sulfonamidobiphenyl-3-ylmethyl)-5H-imidazo[4,5-c]pyridin-4-one is obtained.
Analogously, the compounds
2-isopropyl-5-(3-amidinobenzyl)-3-(3'-sulfonamidobiphenyl-3-ylmethyl)-5H-imidazo[4,5-c]pyridin-4-one and
2-isopropyl-5-(4-amidinobenzyl)-3-(3'-sulfonamidobiphenyl-3-ylmethyl)-5H-imidazo[4,5-c]pyridin-4-one are obtained.

EXAMPLE 11

By reaction of 2-isopropyl-3-[3-(5-methyl-[1,2,4]oxadiazol-3-yl)benzyl]-3,5-dihydroimidazo[4,5-c]pyridin-4-one with 3-cyanophenylboronic acid under copper acetate catalysis in dichloromethane, 2-isopropyl-3-[3-(5-methyl-[1,2,4]oxadiazol-3-yl)benzyl]-5-(3-cyanophenyl)-3,5-dihydroimidazo[4,5-c]pyridin-4-one is obtained. By subsequent reaction in ethanol NaHCO₃ and then with hydroxylammonium chloride, 2-isopropyl-3-[3-(5-methyl-[1,2,4]oxadiazol-3-yl)benzyl]-5-(3-N-hydroxyamidinophenyl)-3,5-dihydroimidazo[4,5-c]pyridin-4-one is obtained.

After hydrogenation analogously to Example 3, 2-isopropyl-3-[3-amidinobenzyl]-5-(3-amidinophenyl)-3,5-dihydroimidazo[4,5-c]pyridin-4-one, FAB 428, is obtained.

Analogously, the compounds below
2-isopropyl-3-[7-(5-methyl-[1,2,4]oxadiazol-3-yl)naphth-2-ylmethyl]-5-(3-cyanophenyl)-3,5-dihydroimidazo[4,5-c]pyridin-4-one,
2-tert-butyl-3-[7-(5-methyl-[1,2,4]oxadiazol-3-yl)naphth-2-ylmethyl]-5-(3-cyanophenyl)-3,5-dihydroimidazo[4,5-c]pyridin-4-one,
2-butyl-3-[7-(5-methyl-[1,2,4]oxadiazol-3-yl)naphth-2-ylmethyl]-5-(3-cyanophenyl)-3,5-dihydroimidazo[4,5-c]pyridin-4-one,
2-isobutyl-3-[7-(5-methyl-[1,2,4]oxadiazol-3-yl)naphth-2-ylmethyl]-5-(3-cyanophenyl)-3,5-dihydroimidazo[4,5-c]pyridin-4-one,
2-isopropyl-3-[7-(5-methyl-[1,2,4]oxadiazol-3-yl)naphth-2-ylmethyl]-5-(4-cyanophenyl)-3,5-dihydroimidazo[4,5-c]pyridin-4-one,
2-tert-butyl-3-[7-(5-methyl-[1,2,4]oxadiazol-3-yl)naphth-2-ylmethyl]-5-(4-cyanophenyl)-3,5-dihydroimidazo[4,5-c]pyridin-4-one,
2-butyl-3-[7-(5-methyl-[1,2,4]oxadiazol-3-yl)naphth-2-ylmethyl]-5-(4-cyanophenyl)-3,5-dihydroimidazo[4,5-c]pyridin-4-one,
2-isobutyl-3-[7-(5-methyl-[1,2,4]oxadiazol-3-yl)naphth-2-ylmethyl]-5-(4-cyanophenyl)-3,5-dihydroimidazo[4,5-c]pyridin-4-one are obtained.

By reaction with hydroxylammonium chloride and subsequent hydrogenation, the diamidino compounds are obtained therefrom.

The following examples relate to pharmaceutical preparations:

Example A

Injection Vials

A solution of 100 g of an active compound of the formula I and 5 g of disodium hydrogenphosphate is adjusted to pH 6.5 in 3 l of double-distilled water using 2N hydrochloric acid, sterile-filtered, dispensed into injection vials, lyophilized under sterile conditions and aseptically sealed. Each injection vial contains 5 mg of active compound.

Example B

Suppositories

A mixture of 20 g of an active compound of the formula I is fused with 100 g of soya lecithin and 1400 g of cocoa butter, poured into moulds and allowed to cool. Each suppository contains 20 mg of active compound.

Example C

Solution

A solution of 1 g of an active compound of the formula I, 9.38 g of NaH₂PO₄.2H₂O, 28.48 g of Na₂HPO₄.12H₂O and 0.1 g of benzalkonium chloride in 940 ml of double-distilled water is prepared. It is adjusted to pH 6.8, made up to 1 l and sterilized by irradiation. This solution can be used in the form of eye drops.

Example D

Ointment 500 mg of an active compound of the formula I is mixed with 99.5 g of petroleum jelly under aseptic conditions.

Example E

Tablets

A mixture of 1 kg of active compound of the formula I, 4 kg of lactose, 1.2 kg of potato starch, 0.2 kg of talc and 0.1 kg of magnesium stearate is compressed to give tablets in a customary manner such that each tablet contains 10 mg of active compound.

Example F

Coated Tablets

Analogously to Example E, tablets are pressed and are then coated in a customary manner using a coating of sucrose, potato starch, talc, tragacanth and colourant.

Example G

Capsules 2 kg of active compound of the formula I are dispensed into hard gelatin capsules in a customary manner such that each capsule contains 20 mg of the active compound.

Example H

Ampoules

A solution of 1 kg of active compound of the formula I in 60 l of double-distilled water is sterile-filtered, dispensed into ampoules, lyophilized under sterile conditions and aseptically sealed. Each ampoule contains 10 mg of active compound.

What is claimed is:

1. A compound of formula I

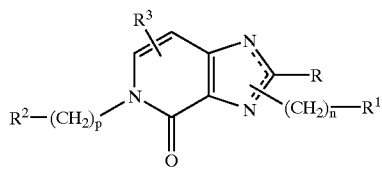

in which

R is H, unbranched or branched alkyl having 1–6 C atoms or cycloalkyl having 3–6 C atoms, $R^1$ is Ar, $R^2$ is Ar', $R^3$ is H, R, $R^4$, Hal, CN, COOH, COOA or $CONH_2$, Ar, Ar' are phenyl, naphthyl or biphenyl, in each case independently of one another unsubstituted or mono-, di- or trisubstituted by R, OH, Hal, CN, $NO_2$, $CF_3$, $NH_2$, NHR, $NR_2$, pyrrolidin-1-yl, piperidin-1-yl, benzyloxy, $SO_2NH_2$, $SO_2NHR$, $SO_2NR_2$, —CONHR, —$CONR_2$, —$(CH_2)_n$—$NH_2$, —$(CH_2)_n$—NHR, —$(CH_2)_n$—$NR_2$, —O—$(CH_2)_n$—$NH_2$, —O—$(CH_2)_n$—NHR, —O—$(CH_2)_n$—$NR_2$, $R^4$ or together by —O—$(CH_2)_m$—O—, $R^4$ is —C(=NH)—$NH_2$ which is unsubstituted or monosubstituted by —COR, —COOR, —OH or by a conventional amino protective group, —NH—C(=NH)—$NH_2$, —C(=O)—N=C($NH_2)_2$,

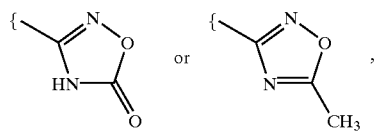

A is alkyl having 1–4 C atoms,

Hal is F, Cl, Br or I, m is 1 or 2, n is 0, 1, 2 or 3, p is 0 or 1, or a salt thereof.

2. A compound according to claim 1, which is
   a) 5-(3-amidinobenzyl)-3-(7-amidinonaphth-2-ylmethyl)-2-isopropyl-3,5-dihydroimidazo-[4,5-c]pyridin-4-one;
   b) 3,5-(bis7-amidinonaphth-2-ylmethyl)-2-isopropyl-3,5-dihydroimidazo[4,5-c]pyridin-4-one;
   or a salt thereof.

3. A process for the preparation of a compound of formula I according to claim 1, or a salt thereof, comprising
   a) liberating one of said compounds from a functional derivative by treating with a solvolysing or hydrogenolysing agent, by
      i) liberating an amidino group from its oxadiazole derivative or oxazolidinone derivative by hydrogenolysis or solvolysis,
      ii) replacing a conventional amino protective group by hydrogen by treating with a solvolysing or hydrogenolysing agent or liberating an amino group protected by a conventional protective group, or
   b) in a compound of the formula I, converting one or more radicals R, $R^1$, $R^2$ and/or $R^3$ into one or more radicals R, $R^1$, $R^2$ and/or $R^3$, by,
      i) hydrolysing an ester group to a carboxyl group
      ii) reducing a nitro group
      iii) acylating an amino group
      iv) converting a cyano group into an amidino group
      and/or
   c) converting a base or acid of formula I into one of its salts.

4. A process for the production of a pharmaceutical preparation comprising combining a compound of formula I according to claim 1 and/or one of its physiologically acceptable salts into a suitable dose form together with at least one solid, liquid or semi-liquid excipient or auxiliary.

5. A pharmaceutical composition comprising at least one compound of formula I according to claim 1 and/or a physiologically acceptable salt, thereof, and a pharmaceutically acceptable carrier.

6. A method for the treatment of thromboses, myocardial infarct, arteriosclerosis, inflammations, apoplexy, angina pectoris, restenosis after angioplasty or intermittent claudication, comprising administering to a host in need thereof an effective amount of a compound of formula I according to claim 1, or a physiologically acceptable salt thereof.

7. A method for the inhibition of coagulation factor Xa, comprising administering to a host in need thereof an effective amount of a compound of formula I according to claim 1, or a physiologically acceptable salt thereof.

* * * * *